United States Patent [19]

Monkiewicz et al.

[11] Patent Number: 5,646,325
[45] Date of Patent: Jul. 8, 1997

[54] PROCESS FOR THE PREPARATION OF 3-ACRYLOYLOXYPROPYLALKOXYSILANES

[75] Inventors: Jaroslaw Monkiewicz; Albert Frings; Michael Horn; Peter Jenkner; Hans-Joachim Koetzsch; Frank Kropfgans; Claus-Dietrich Seiler, all of Rheinfelden; Hans-Guenther Srebny, Duelmen-Rorup; Burkhard Standke, Loerrach, all of Germany

[73] Assignee: Huels Aktiengesellschaft, Marl, Germany

[21] Appl. No.: 533,313

[22] Filed: Sep. 25, 1995

[30] Foreign Application Priority Data

Sep. 24, 1994 [DE] Germany ............... 44 34 200.4

[51] Int. Cl.$^6$ ............................. C07F 7/08; C07F 7/18
[52] U.S. Cl. .................................................. 556/440
[58] Field of Search ......................................... 556/440

[56] References Cited

U.S. PATENT DOCUMENTS

| | | |
|---|---|---|
| 5,103,032 | 4/1992 | Turner et al. |
| 5,142,037 | 8/1992 | Yamazaki et al. ............ 556/440 X |
| 5,214,077 | 5/1993 | Herzig et al. ............... 556/440 X |
| 5,493,039 | 2/1996 | Okawa et al. ............... 556/440 |

FOREIGN PATENT DOCUMENTS

| | | |
|---|---|---|
| 0 247 501 | 2/1987 | European Pat. Off. |
| 0 277 023 | 8/1988 | European Pat. Off. |
| 0 472 438 | 2/1992 | European Pat. Off. |
| 0 562 584 | 9/1993 | European Pat. Off. |

OTHER PUBLICATIONS

Chemical Abstracts, vol. 84, No. 23, p. 490, Jun. 7, 1976, AN–84:165010a, JP–75 24,947, Aug. 20, 1975.

Chemical Abstracts, vol. 114, No. 7, p. 698, Feb. 18, 1991, AN–114: 62165p.

Chemical Abstracts, vol. 119, No. 17, p. 815, Oct. 25, 1993, AN–119: 181012z, PL–158567, Sep. 30, 1992.

*Primary Examiner*—Paul F. Shaver
*Attorney, Agent, or Firm*—Oblon, Spivak, McClelland, Maier & Neustadt, P.C.

[57] ABSTRACT

3-Acryloyloxypropylalkoxysilanes of formula I:

$$CH_2=C(R)C(O)O(CH_2)_3Si(R^1)_a(OR^2)_{3-a} \qquad (I)$$

are prepared by reacting a hydridosilane of formula II:

$$HSi(R^1)_a(OR^2)_{3-a} \qquad (II)$$

with an allyl ester of formula III:

$$CH_2=C(R)C(O)OCH_2CH=CH_2 \qquad (III),$$

where R is a hydrogen atom or a methyl group, $R^1$ and $R^2$ are each $C_1$ to $C_6$ alkyl groups or phenyl groups, and a is 0, 1 or 2, in the presence of a platinum catalyst.

19 Claims, No Drawings

PROCESS FOR THE PREPARATION OF 3-ACRYLOYLOXYPROPYLALKOXYSILANES

BACKGROUND OF THE INVENTION

1. Field of the Invention

The invention relates to a process for the preparation of 3-acryloyloxypropylalkoxysilanes.

2. Description of the Background

3-Acryloyloxypropylalkoxysilanes, especially the 3-methacryloyloxypropylalkoxysilanes, are among the organic silanes which are used on a large scale in industry. Since their structure includes both a hydrolysis-sensitive alkoxysilyl group, which can enter into a stable bond with inorganic materials, and a double bond which is active towards the organic reactants, the 3-acryloyloxypropylalkoxysilanes lend themselves to a wide variety of possible applications, for example, as coupling agents. 3-Methacryloyloxypropyltrimethoxysilane is frequently also used for modifying surfaces in the glass fibre industry.

It is known that various platinum compounds can be employed as catalysts for direct reaction of hydridosilanes with the allyl esters of acrylic and methacrylic acid. The catalyst system most frequently employed in industry for this hydrosilylation reaction is homogeneous and comprises hexachloroplatinic acid in acetone or isopropanol. The use of this high-chlorine platinum(IV) compound for the preparation of 3-methacryloyloxy- and 3-acryloyloxypropylalkoxysilanes is described in EP-A 0 277 023, EP-B 0 247 501 and EP-A 0 472 438.

EP-B 0 247 501 discloses a number of platinum(II) complexes as possible alternative catalysts of hexachloroplatinic acid, dichlorobis(acetonitrile)platinum(II), dichlorobis(ethylene)platinum(II), cis-dichlorobis(triphenylphosphino)platinum(II) and a platinum(O) complex-tetrakis(triphenylphosphino)platinum(O).

A further chlorine-containing platinum(II) catalyst, dichloro(1,5-cyclooctadiene)platinum(II), and another platinum(O) catalyst, 1,3-divinyltetramethyldlsiloxane/platinum complex in toluene, are disclosed in EP-A 0 472 438 for the direct reaction of allyl methacrylates with trialkoxysilanes.

The yields disclosed in the above-mentioned prior art for the preparation of 3-acryloyloxy- and 3-methacryloyloxy-propylalkoxysilanes, using the chlorine-containing platinum catalysts mentioned and taking into account the particular reaction regime, are in the range from 75 to 88%. The prior art processes require laborious working up of the crude product formed.

The use of the prior art catalysts, moreover, because of their high chlorine content, which may amount to as much as 50% or more of their molecular weight, must be considered in relationship to the environment. Furthermore, these chlorine-containing catalyst systems must be employed as highly dilute solutions in acetone or isopropanol.

A considerable problem in all of the prior art processes is the unwanted tendency of the final products to polymerize. According to the teaching of EP-A 0 472 438, the tendency of the products to polymerize can be prevented by addition of sterically hindered phenols, amines, amides and aminophenols to the reaction mixture. In most cases the commercially available polymerization inhibitors are employed in quantities of from 1 to 5,000 equivalents of the platinum catalyst. Furthermore, it is possible, by continuous introduction of a gas containing molecular oxygen, to suppress polymerization. A gas mixture of this kind normally contains from around 0.1 to 20% by volume of oxygen.

From the literature it is known that the majority of hydrosilylation reactions proceed via a catalytically active species with platinum in oxidation states (II) and (IV). Even tetrakis(triphenylphosphine)platinum(O) has not acquired any great economic importance because of its instability towards oxygen, resulting in a relatively long induction period in the hydrosilylation, and because of its markedly lower activity and chemoselectivity in the reaction of allyl compounds with hydridosilanes.

The chlorine-free catalyst disclosed in EP-A 0 472 438-1,3-divinyltetramethylsilane/platinum complex, which contains platinum in oxidation state (0), can likewise be employed only as a dilute solution and, furthermore, is stable only for a limited time. Its activity and selectivity with regard to allyl compounds and acrylic compounds, furthermore, is inadequate for industrial purposes. A need therefore continue to exist for an economically more favorable catalytic process for preparing 3-acryloyloxypropylalkoxysilanes with minimal environmental impact.

SUMMARY OF THE INVENTION

Accordingly, one object of the invention is to provide a process of minimal environmental impact, which is at the same time economic, for the preparation of 3-acryloyloxypropylalkoxysilanes.

Briefly, this object and other objects of the present invention as hereinafter with become more readily apparent can be attained in a process for preparing 3-acryloyloxypropylalkoxysilanes of formula I:

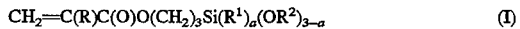

$$CH_2=C(R)C(O)O(CH_2)_3Si(R^1)_a(OR^2)_{3-a} \quad (I)$$

by reacting a hydridosilane of formula II:

$$HSi(R^1)_a(OR^2)_{3-a} \quad (II)$$

with an allyl ester of formula III:

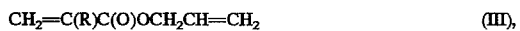

$$CH_2=C(R)C(O)OCH_2CH=CH_2 \quad (III),$$

where R is a hydrogen atom or a methyl group, $R^1$ and $R^2$ may be $C_1$ to $C_6$ alkyl groups or phenyl groups, and a is 0, 1 or 2, in the presence of a halogen-free platinum catalyst containing platinum in oxidation state +2.

DETAILED DESCRIPTION OF THE PREFERRED EMBODIMENTS

Surprisingly it has now been found that the reaction of a hydridosilane II with an allyl ester III in the presence of a halogen-free platinum catalyst containing platinum in oxidation state +2 makes it possible, in a particularly economic and environmentally compatible process, to prepare 3-acryloyloxypropylalkoxysilanes. Moreover, the bis(acetylacetonato)platinum(II) complex, for example, which is employed in the preparation as a chlorine-free catalyst, is also readily accessible on an industrial scale and can in addition be stored for a relatively long time without loss of activity.

Halogen-free platinum catalysts with the oxidation state +2, which are preferably employed for the process according to the invention, are platinum(II) cyanide, bis(phthalocyaninato)platinum(II), bis(trialkylphosphine)platinum(II) oxalate, tetraamineplatinum(II) nitrate, bis(acetylacetonato)triphenylphosphineplatinum(II), bia (acetonato)bis(triphenylphosphine)platinum(II), bis(acetylacetonato)trialkylphosphineplatinum(II), bio(acetonato)bis(trialkylphosphine)platinum(II), bis(acetylacetonato)pyridineplatinum(II), bis(acetonato)bis(pyridine)platinum(II), potassium tetracyanoplatinate(II), bis(triphenylphosphino)bis(phenyl)platinum(II), bio(triphenylphosphino)bis(alkyl)platinum(II), dimethyl(1,5-cyclooctadiene)platinum (II) or bis(acetylacetonato)platinum(II) or mixtures thereof. As the halogen-free platinum catalyst it is particularly preferred to employ bis(acetylacetonato)platinum(II). The halogen-free platinum catalyst containing platinum in oxidation state +2, especially bis(acetylacetonato)platinum(II), can be employed either in the absence or in the presence of phosphorus and/or nitrogen-containing ligands. Suitable phosphorus- and nitrogen-containing ligands include triphenylphosphine, triethylamine and ethylenediamine.

The reaction can either be carried out without solvent or in the presence of a solvent. If the reaction is carried out in the presence of a solvent, the solvent employed should be inert with respect to the starting materials and should thus be, for example, toluene, hexane, methanol or methyl tert-butyl ether. The solvent-free process variant is of particular environmental compatibility.

The concentration of platinum employed in the reaction, based on the quantity of starting materials, is normally from 5 to 500 ppm by weight, preferably from 10 to 200 ppm by weight and particularly preferably from 20 to 100 ppm by weight.

Increasing the catalyst concentration has the general effect of reducing the reaction time. Depending on the concentration of platinum, the reaction time normally ranges from 15 minutes and 24 hours.

In the process according to the invention, the reaction can also be carried out in the presence of polymerization inhibitors. Suitable polymerization inhibitors include a sterically hindered phenol and/or an oxygen-containing gas which is passed into the reaction mixture during the reaction. It is preferred to employ 2,6-di-tert-butylphenol as polymerization inhibitor. An oxygen-containing gas, for example, air or, as is preferred for reasons of safety, a nitrogen/air mixture, which can be passed into the reaction mixture, has the general effect, in addition, of suppressing polymerization of the product.

For effective reduction of the unwanted formation of polymer, the concentration of polymerization inhibitor employed in the reaction, based on the quantity of the starting materials, is preferably from 0.25 to 3.00 mol %, particularly preferably from 0.8 to 1.0 mol %.

The present process can be carried out either continuously or batchwise. The reaction is normally carried out at temperatures of from 60 to 130° C., preferably at temperatures from 70 to 110° C. The batchwise procedure can be carried out in a variety of ways, for example by placing the catalyst with the inhibitor in an allyl ester, as an initial charge and to the reactor, and then adding the hydridosilane to the reactor, or else metering the two reactants with the catalyst and the inhibitor simultaneously into the reactor and bringing the mixture to the desired reaction temperature. A further possibility is to introduce the hydridosilane, as the initial charge into the reactor, and then add the allyl ester to the reactor.

Hydridosilanes which can be employed in the present process are silanes with various patterns of substitution which have at least one H—Si group in their structure. As hydridosilanes it is preferred to employ a trialkoxysilane, with particular preference being given to hydridosilanes particularly trimethoxysilane, triethoxysilane, dimethoxymethylsilane, diethoxymethylsilane, ethoxydimethylsilane or methoxydimethylsilane. The allyl ester employed is preferably allyl methacrylate.

The advantages which can be achieved by the present process result from the fact that, instead of the less efficient and environmentally suspect, chlorine-containing platinum catalysts, a halogen free, environmentally friendly platinum catalyst containing platinum in oxidation state +2 can be employed. This brings about a drastic reduction in the halogen content of the end product, and the corrosion risks in the production plant are minimized, which advantages contribute to a more favorable environmental impact. Moreover, the present process provides a more economic mode of operation. In the present operation, the catalyst system employed is stable even over a relatively long period. A solvent-free process variant is particularly environmentally favorable. The chlorine-free platinum(II) complex catalysts employed in the present process have the effect, in the reaction, of bringing about a high chemoselectivity and high conversion rates. The high purity of the crude product obtained in the present process makes it possible to obtain the 3-acryloyloxypropylalkoxysilane, while expending a relatively small amount of resources on distillation.

Having generally described this invention, a further understanding can be obtained by reference to certain specific examples which are provided herein for purposes of illustration only and are not intended to be limiting unless otherwise specified.

EXAMPLE 1

17.9 g (0.146 mol) of trimethoxysilane (TMOS), 1.2 mg of platinum(II) acetylacetonate (1.0 ml of a solution in TMOS, approximately 15 ppm of Pt based on the starting materials) and 580 mg of 2,6-di-tert-butylphenol are placed in a 100 ml three-necked flask fitted with magnetic stirrer, condenser, thermometer and dropping funnel. The contents of the flask are heated with stirring to about 90° C., and at this temperature 18.3 g (0.143 mol) of allyl methacrylate are added dropwise at a rate such that the temperature does not exceed 95° C. Following the addition of the ester, the reaction mixture is stirred at 90° C. for a further 5 hours. During the reaction, air is passed into the reaction mixture via a glass capillary. The conversion, determined gas chromatographically, is about 96% for allyl ester and more than 99% for TMOS. The selectivity of the 3-methacryloyloxypropyltrimethoxysilane is 88%.

EXAMPLE 2

18.87 g (0.15 mol) of trimethoxysilane (TMOS), 5.8 mg of platinum(II) acetylacetonate (about 75 ppm of Pt based on the starting materials), 4.0 mg of triphenylphosphine (Pt/P= 1/1) and 580 mg of 2,6-di-tert-butylphenol are placed in a 100 ml three-necked flask fitted with magnetic stirrer, condenser, thermometer and dropping funnel. The contents of the flask are heated with stirring to about 80° C., and at this temperature 18.33 g (0.143 mol) of allyl methacrylate are added dropwise at a rate such that the temperature does not rise above 90° C. Following the addition of the ester, the reaction mixture is stirred at 90° C. for a further 4 hours. During the reaction, air is passed into the reaction mixture via a glass capillary. The conversion, calculated from the gas chromatogram, is about 97% for allyl ester and more than 99% for TMOS. The selectivity of the 3-methacryloyloxypropyltrimethoxysilane is 87%.

EXAMPLE 3

The procedure described in Example 2 is followed. Instead of triphenylphosphine, 11 µl of triethylamine are employed. The conversion, calculated by gas chromatogram, is about 98% for allyl ester and more than 99% for TMOS. The selectivity of the 3-methacryloyloxypropyltrimethoxysilane is 87%.

EXAMPLE 4

22.8 g (0.139 mol) of triethoxysilane (TEOS), 3.0 mg of platinum(II) acetylacetonate (2 ml of solution in TEOS, about 30 ppm of Pt based on the starting materials) and 570 mg of 2,6-di-tert-butylphenol are placed in a 100 ml three-necked flask fitted with magnetic stirrer, condenser, thermometer and dropping funnel. The contents of the flask are heated to about 100° C. with stirring, and 18.3 g (0.143 mol) of allyl methacrylate are added dropwise at a rate such that the temperature does not exceed 110° C. Following the addition of the ester, the reaction mixture is stirred at 100° C. for about 4 hours more. During the reaction, air is passed into the reaction mixture via a glass capillary. The conversion, calculated from the gas chromatogram, is about 94% for allyl ester and more than 99% for TEOS. The selectivity of the 3-methacryloyloxypropyltriethoxysilane is 85%.

EXAMPLE 5

20.43 g (0.15 mol) of methyldiethoxysilane, 6.2 mg of platinum(II) acetylacetonate (about 75 ppm of Pt based on the starting materials) and 590 mg of 2,6-di-tert-butylphenol are placed in a 100 ml three-necked flask fitted with magnetic stirrer, condenser, thermometer and dropping funnel. The contents of the flask are heated to about 100° C. with stirring, and 18.33 g (0.143 mol) of allyl methacrylate are added dropwise at a rate such that the temperature does not exceed 110° C. Following the addition of the ester, the reaction mixture is stirred at 100° C. for about 2 hours more. During the reaction, air is passed into the reaction mixture via a glass capillary. The conversion, calculated from the gas chromatogram, is about 94% for allyl ester and more than 99% for methyldiethoxysilane. The selectivity of the 3-methacryloyloxypropylmethyldiethoxysilane is 80%.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the preparation of 3-acryloyloxypropylalkoxysilanes of formula I:

$$CH_2=C(R)C(O)O(CH_2)_3Si(R^1)_a(OR^2)_{3-a} \quad (I)$$

comprising: reacting a hydridosilane of formula II:

$$HSi(R^1)_a(OR^2)_{3-a} \quad (II)$$

with an allyl ester of formula III:

$$CH_2=C(R)C(O)OCH_2CH=CH_2 \quad (III),$$

where R is a hydrogen atom or a methyl group, $R^1$ and $R^2$ are each $C_1$ to $C_6$ alkyl groups or phenyl groups, and a is 0, 1 or 2, in the presence of a halogen-free platinum catalyst containing platinum in oxidation state +2.

2. The process according to claim 1, wherein the halogen-free platinum catalyst employed is platinum(II) cyanide, bis(phthalocyaninato)platinum(II), bis(trialkylphosphine) platinum(II) oxalate, tetraamineplatinum(II) nitrate, bis(acetylacetonato)triphenylphosphineplatinum(II), bis(acetonato)bis(triphenylphosphine)platinum(II), bis(acetylacetonato)trialkylphosphineplatinum(II), bis(acetonato)bis(trialkylphosphine)platinum(II), bis(acetylacetonato)pyridineplatinum(II), bis(acetonato)bis(pyridine)platinum(II), potassium tetracyanoplatinate(II), bis(triphenylphosphino)bis(phenyl)platinum(II), bis(triphenylphosphino)bis(alkyl)platinum(II), dimethyl(1,5-cyclooctadiene)platinum(II) or bis(acetylacetonato)platinum(II) or mixtures thereof.

3. The process according to claim 2, wherein bis(acetylacetonato)platinum(II) is employed as halogen-free platinum catalyst.

4. The process according to claim 1, wherein the halogen-free platinum catalyst containing platinum in oxidation state +2 is employed in the presence of phosphorus- and/or nitrogen-containing ligands.

5. The process according to claim 1, wherein the reaction is carried out in the presence of a solvent.

6. The process according to claim 1, wherein the reaction is carried out without solvent.

7. The process according to claim 1, wherein the concentration of platinum employed in the reaction, based on the quantity of starting materials, is from 5 to 500 ppm by weight.

8. The process according to claim 7, wherein the concentration of platinum employed in the reaction, based on the quantity of starting materials, is from 10 to 200 ppm by weight.

9. The process according to claim 8, wherein the concentration of platinum employed in the reaction, based on the quantity of starting materials, is from 20 to 100 ppm by weight.

10. The process according to claim 1, wherein the reaction is carried out in the presence of polymerization inhibitors.

11. The process according to claim 1, wherein a sterically hindered phenol and/or an oxygen-containing gas which is passed into the reaction mixture during the reaction, is employed as polymerization inhibitor.

12. The process according to claim 9, wherein 2,6-di-tert-butylphenol is employed as polymerization inhibitor.

13. The process according to claim 9, wherein the concentration of polymerization inhibitor employed in the reaction, based on the quantity of starting materials, ranges from 0.25 to 3.00 mol %.

14. The process according to claim 13, wherein the concentration of polymerization inhibitor employed in the reaction, based on the quantity of starting materials, is from 0.8 to 1.0 mol %.

15. The process according to claim 9, wherein the reaction is carried out at temperatures of from 60° to 130° C.

16. The process according to claim 15, wherein the reaction is carried out at temperatures of from 70° to 110° C.

17. The process according to claim 1, wherein a trialkoxysilane is employed as hydridosilane.

18. The process according to claim 17, wherein trimethoxysilane, triethoxysilane, dimethoxymethylsilane, diethoxymethylsilane, ethoxydimethylsilane or methoxydimethylsilane is employed as hydridosilane.

19. The process according to claim 1, wherein allyl methacrylate is employed as allyl ester.

* * * * *